(12) United States Patent
Tatebe et al.

(10) Patent No.: US 8,034,301 B2
(45) Date of Patent: Oct. 11, 2011

(54) TEST PAPER AND POROUS MEMBRANE

(75) Inventors: Ken Tatebe, Kanagawa (JP); Katsuyuki Ooba, Yamanashi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/943,053

(22) Filed: Nov. 10, 2010

(65) Prior Publication Data

US 2011/0062616 A1  Mar. 17, 2011

Related U.S. Application Data

(62) Division of application No. 10/551,279, filed as application No. PCT/JP2004/004024 on Mar. 24, 2004.

(30) Foreign Application Priority Data

Mar. 27, 2003 (JP) ................................. 2003-087812
Nov. 10, 2003 (JP) ................................. 2003-379492

(51) Int. Cl.
*B01D 11/04* (2006.01)
*B01D 63/00* (2006.01)
*B01D 25/00* (2006.01)
*B01D 67/00* (2006.01)
*G01N 1/18* (2006.01)
*B05D 5/00* (2006.01)

(52) U.S. Cl. ................... 422/255; 422/617; 210/321.64; 210/323.1; 210/331; 210/348; 436/178; 427/244; 264/48

(58) Field of Classification Search .................. 422/56, 422/57, 101, 255, 617; 210/321.64, 323.1, 210/331, 346, 348; 436/178; 427/244; 264/48
See application file for complete search history.

(56) References Cited

U.S. PATENT DOCUMENTS 5,968,836 A    10/1999 Matzinger et al.

FOREIGN PATENT DOCUMENTS

| EP | 0926484 A2 | 6/1999 |
|---|---|---|
| JP | 11-183474 A | 7/1999 |
| JP | 2001-164029 A | 6/2001 |
| JP | 2001-164030 A | 6/2001 |
| JP | 2001-165930 * | 6/2001 |
| JP | 2001-165930 A | 6/2001 |
| WO | WO 98/25758 A1 | 6/1998 |
| WO | WO 9825758 A1 * | 6/1998 |

\* cited by examiner

*Primary Examiner* — Jill Warden
*Assistant Examiner* — Dean Kwak
(74) *Attorney, Agent, or Firm* — Buchanan Ingersoll & Rooney PC

(57) ABSTRACT

A test paper includes a porous membrane capable of separating an object that should be filtered out of a sample by filtration, the porous membrane carrying a reagent capable of reacting with a specified component of the sample to result in coloring. The porous membrane includes a first layer having a surface on which the sample is supplied and a second layer having a surface at which sample percolation and measuring are effected, the first layer composed of large pore portions, the surface of the first layer consisting of a smooth surface having open pore portions, the second layer composed of minute pore portions the surface of the second layer consisting of a surface having open pore portions. The porous membrane has a thickness of 50 to 200 μm and a porosity of 60 to 95%.

8 Claims, 3 Drawing Sheets

TEST PAPER AND POROUS MEMBRANE

CROSS REFERENCE TO RELATED APPLICATIONS

This application is a Divisional of U.S. application Ser. No. 10/551,279, filed Sep. 27, 2005, which is the National Stage of International Application No. PCT/JP2004/004024, filed Mar. 24, 2004, the disclosures of both of which are incorporated herein by reference in their entirety, and claims priority to Japanese Patent Application Nos. 2003-087812, filed Mar. 27, 2003 and 2003-379492, filed Nov. 10, 2003, the disclosures of both of which are incorporated herein by reference in their entirety.

TECHNICAL FIELD

This invention relates to a test paper for measuring an amount of a specified component in a sample such as, for example, for measuring a blood glucose level, and also to a porous membrane used therefor.

BACKGROUND ART

Blood glucose meters (measuring devices of a component in the blood) for carrying out measurement of a blood glucose level are known. The blood glucose meter is one wherein a blood glucose level is quantitatively determined by optically measuring (color measuring) a degree of a color change of a test paper that is colored depending on the amount of glucose (grape sugar) in the blood. The color measurement of the test paper is carried out at a photometric unit provided with a light emission element and a light receiving element wherein light is irradiated on the test paper to measure an intensity of reflected light.

With such a blood glucose meter, after operations of supplying the blood (sample) to a test paper and developing thereat, the measurement of a blood glucose level is started, and this presents a problem in that since a time required from the supply of the blood to the test paper till the color measurement is not constant, an measuring error may be caused thereby. To avoid this, there is a demand for development of an automatic blood glucose meter capable of continuously, automatically performing a series of operations covering from supply and development to a test paper to measurement.

On the other hand, for the test paper, there is known a porous membrane having such an arrangement that a reagent is carried on a sheet substrate constituted of a porous material capable of absorbing a sample therein. This type of test paper is low in transmissivity, i.e. developability, because the micro pores in the sheet substrate are so small in size as about 0.5 μm, with the problem that it takes a long time for the development of a sample. The long time required for the development of a sample in this way is inconvenient for such an automatic blood glucose meter as mentioned above.

Where an isotropic, porous membrane whose pore size is uniform throughout the membrane is used as a test paper, an object that should be filtered out in a sample is removed at a membrane surface, thus presenting the problem that it takes a long time for the development of the sample. Slow development of the sample does not allow the sample in a small amount to be percolated up to a measuring surface, with the attendant problem that a sample to be supplied increases in amount.

As to an isotropic porous membrane, unless the membrane is completely isotropic, developing rates of a sample at opposite sides differ from each other, and thus, it becomes necessary to deal with such a membrane as having front-back both sides. In this connection, however, it is usual that the front and back sides of the membrane are not visibly discriminated from each other, so that when a slight degree of anisotropy is caused in the membrane upon manufacturing an isotropic, porous membrane, a problem arises in that measuring accuracy is influenced.

For measures for solving such problems as set out hereinabove, the present applicant has proposed test papers (see Japanese Patent Laid-open No. Hei 11-183474) including (1) a test paper laminating a first porous layer carrying a reagent capable of giving a color by reaction with a specified component in a sample, and a second porous layer having a function of separating an object that should be filtered out from the sample by filtration, wherein the sample is supplied from a side of the first layer, (2) a test paper as recited in (1) above, wherein the first layer and the second layer are, respectively, hydrophilic, (3) a test paper as recited in (1) or (2) above, wherein micro pores in the first layer have a size of 8 to 50 μm, (4) a test paper as recited in any one of (1) to (3) above, wherein micro pores in the second layer have a size of not larger than 5 μm, and (5) a test paper as recited in any one of (1) to (4) above, wherein the sample is made of blood and the object that should be filtered out is blood cells mainly composed of blood red cells.

The present applicant has also proposed a test paper (see Japanese Patent Laid-open No. 2001-164030) made of a porous membrane which has an average pore size ranging 0.1 to 2 μm, a thickness of 5 to 200 μm and a porosity of 50 to 95% and which is anisotropic in such a way that a ratio between average pore sizes in one surface and the other surface is 1.5 or over.

However, where the test paper set out in the Japanese Patent Laid-open No. Hei 11-183474 is used, the lamination step of the first and second layers are necessary, thus making the manufacturing process complicated. Moreover, where the test paper described in the Japanese Patent Laid-open No. 2001-164030 is used, it is required to rapidly develop a blood plasma component reacted with a reagent toward a measuring surface while filtering out blood cells, with the following problems being involved. More particularly, a smaller size is more effective for separation and removal of blood cells by filtration, and too small a pore size leads to slow development of a blood plasma component. In addition, when blood cells are removed while keeping a given developing rate by making a large pore size at an inlet of the sample and a small pore size at an outlet thereof, hemoglobin in the blood cell component becomes visible through the porous structure if the blood cell removal is carried out just beneath the measuring surface, thereby giving an influence on measurement accuracy. In addition, when portions having pores of large size are large in area, a surface area is lessened, thus having one unable to sufficiently carry a reagent necessary for the measurement.

DISCLOSURE OF INVENTION

The invention has for its object the provision of a test paper which can solve many problems stated hereinabove, is able to shorten a time required for development of samples and is high in measurement accuracy and also a porous membrane used therefor.

We have found that a porous membrane and a test paper, which, respectively, have a function of separating an object that should be filtered out from a sample by filtration, and carry thereon a reagent capable of giving a color through reaction with a specific component in the sample, and have specific types of layers therein, can solve the afore-stated problems, shorten a time required for development of a sample, and exhibit high measurement accuracy, thus arriving at the completion of the invention.

More particularly, the invention contemplates to provide a test paper recited in (1) to (5) below and a porous membrane used therefor and recited in (6) to (9) below.

(1) A test paper including a porous membrane having a function of separating an object that should be filtered out from a sample by filtration and carrying therein a reagent capable of giving a color by reaction with a specified component in the sample, wherein the porous membrane has a first layer having a surface to which a sample is supplied and a second layer having a surface at which the sample is percolated and measured, the first layer being made of large-sized pore portions, with a surface of the first layer being a smooth surface having apertures thereat, the second layer being made of small-sized pore portions, with a surface of the second layer having apertures thereat, a boundary between the first layer and the second layer being located from the surface of the first layer within a range of 1/5 to 1/2 of a thickness of the porous membrane, and wherein the porous membrane has a thickness of 50 to 200 μm and a porosity of 60 to 95%, the first layer has an average pore size of 0.5 to 10 μm in the surface thereof, and the second layer has an average pore size of 0.1 to 3.0 μm in the surface thereof.

(2) The test paper as recited in (1) above, wherein the second layer has a surface glossiness of not higher than 11.

(3) The test paper as recited in (1) or (2), wherein the second layer has an irregular surface to provide a gloss and luster-free surface.

(4) The test paper as recited in any one of (1) to (3) above, wherein a material for the porous membrane is made of polyether sulfone.

(5) The test paper as recited in any one of (1) to (4) above, wherein the sample is a blood and the object that should be filtered out contains blood cells.

(6) A porous membrane which includes first layer having a surface and a second layer having another surface, wherein the first layer is made of large-sized pore portions, with a surface of the first layer being a smooth surface having apertures thereat, the second layer is made of small-sized pore portions, with a surface of the second layer having apertures thereat, and a boundary between the first layer and the second layer is located from the surface of the first layer within a range of 1/5 to 1/2 of a thickness of the porous membrane, and wherein a thickness ranges 50 to 200 μm, a porosity ranges 60 to 95%, the first layer has an average pore size of 0.5 to 10 μm in the surface thereof, and the second layer has an average pore size of 0.1 to 3.0 μm in the surface thereof.

(7) The porous membrane as recited in (6) above, wherein a ratio between the average size in the surface of the first layer and the average size in the surface of the second layer is in the range of 1 to 6.

(8) The porous membrane as recited in (6) or (7), wherein the second layer has a surface glossiness of not higher than 11.

(9) The porous membrane as recited in any one of (6) to (8), wherein the second layer has an irregular surface to provide a gloss and luster-free surface.

BEST MODE FOR CARRYING OUT THE INVENTION

Figure 1:
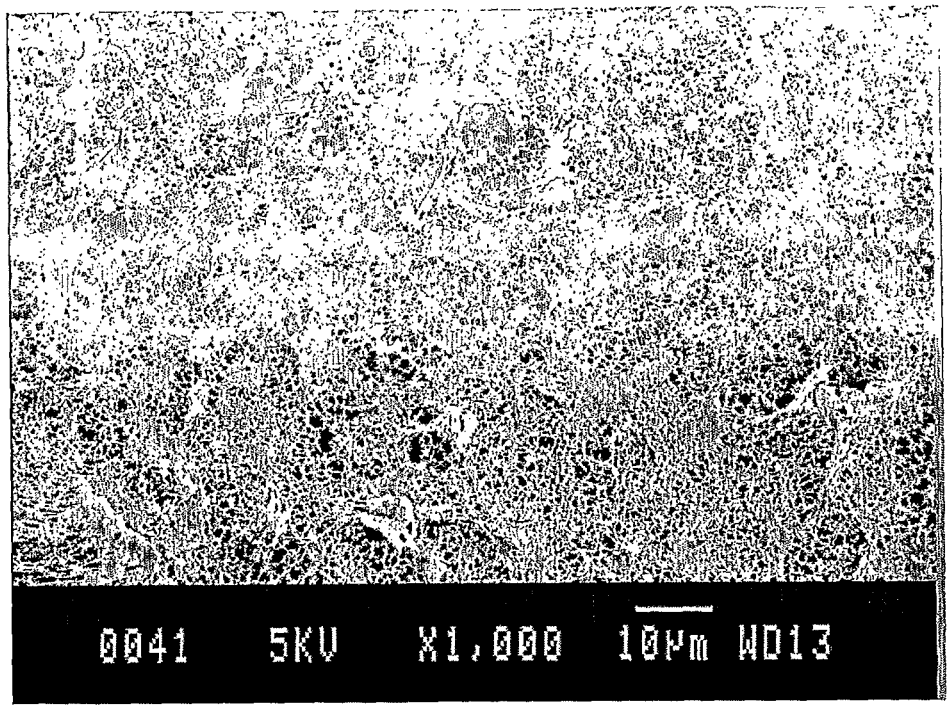
FIG. 1 is an electron micrograph showing a surface of a second layer of a porous membrane obtained in Example 3.

The test paper of the invention is one which comprises a porous membrane having a function of separating an object that should be filtered out from a sample by filtration and carrying thereon a reagent capable of giving a color by reaction with a specified component in the sample, wherein the porous membrane has a first layer having a surface to which a sample is supplied and a second layer having a surface at which the sample is percolated and measured, the first layer being made of large-sized pore portions, with a surface of the first layer being a smooth surface having apertures thereat, the second layer being made of small-sized pore portions, with a surface of the second layer having apertures thereat, and a boundary between the first layer and the second layer being located from the surface of the first layer within a range of 1/5 to 1/2 of a thickness of the porous membrane, and wherein the porous membrane has a thickness of 50 to 200 μm and a porosity of 60 to 95%, the first layer has an average pore size of 0.5 to 10 μm in the surface thereof, and the second layer has an average pore size of 0.1 to 3.0 μm in the surface thereof.

The porous membrane constituting the test paper of the invention is described in detail.

As stated above, the porous membrane has the function of separating an object that should be filtered out from a sample by filtration, and carries a reagent capable of giving a color by reaction with a specified component in the sample.

The samples include, for example, blood, urea, sweat, lymph fluid, bile, saliva and the like.

Although depending on the type of sample, specified components in the sample include glucose, cholesterol, hemoglobin, lactic acid, hemoglobin ATC, ketone body and the like.

For the object that should be filtered out in case where the sample is blood, mention is a blood cell component such as blood red cell.

Where the test paper of the invention is used for measurement of a blood glucose level, preferred examples of the reagent include enzymes such as glucose oxidase (GOD), peroxidase, (POD), ascorbic acid oxidase, alcohol oxidase, cholesterol oxidase and the like, coloring reagents such as 4-aminoantipyrine, N-ethyl-N-(2-hydroxy-3-sulfopropyl)-m-toluidine and the like, and buffering agents such as a phosphate buffering agent.

The amount (μg/cm$^2$) of the reagent in the porous membrane relates with reactivity with such a specified component as indicated above and is in the range of 80 to 2400 μg/cm$^2$, preferably 168 to 1260 μg/cm$^2$. This range is favorable for the reason that a color change occurs linearly from a low blood glucose level to a high blood glucose level.

The porous membrane forming the test paper of the invention has, as stated hereinbefore, a first layer having a surface to which a sample is supplied, and a second layer having a surface at which the sample is percolated and measured, the first layer being made of large-sized pore portions, with a surface of the first layer being a smooth surface having apertures thereat, the second layer being made of small-sized pore portions, with a surface of the second layer being one having apertures thereat.

In present description, the large-sized pore portion and the small-sized pore portion are defined as follows. When the porous membrane is divided into a desired number of part (e.g. ten divisions) along the thickness thereof, the large-sized pore portion is a membrane portion wherein the section density is 40% or below and the small-sized pore portion is a membrane portion wherein the section density exceeds 40%. The measurement of the section density is carried out such that a membrane portion of an electron micrograph at a magnification of 1500 of a section of the porous membrane is taken in a scanner at 300 dpi on a 8 bits gray scale, the resulting image is binarized while taking an average value of scale values containing 5% of black element from a black color side and also from white color side as a border line, thereby determining a ratio of the white element as a section density.

The aperture means a pore opened at the surface of the porous membrane, and the surface of the second layer should preferably have a glossiness of not higher than 11, preferably 3 to 10, more preferably 3 to 8. When the surface of the second layer has a glossiness within the above-defined range, the surface of the second layer has irregularities and is in a gloss and luster-free state. As will be described hereinafter, for measurement of a reflection absorbance, direct light reflected from the surface serves as a noise, and thus, the surface of the second layer should preferably have irregularities and be in a gloss and luster-free state.

This is now described in more detail.

A chronometer for colorimetrically measuring a test paper acts to irradiate light for measurement against a test paper and sense a quantity of light returned by reflection. The ratio between the quantities of the irradiated light and the light returned by reflection becomes reflectivity. With such a measuring instrument as mentioned above, a sample concentration is measured by utilizing a ratio between the reflectivity of a test paper prior to addition of a sample (white reflectivity) and the reflectivity of the test paper after addition of the sample and coloration with a reagent (color reflectivity), and an analytical curve established in relation to a sample concentration (i.e. a relation expressed according to the following equation) in case where light having a given wavelength (e.g. 605 to 610 nm) is applied to the test paper.

Reflectivity ratio=white reflectivity/color reflectivity ∝ sample concentration

It will be noted that a higher sample concentration results in a lower color reflectivity, thus leading to a larger reflectivity ratio. In this condition, when the measuring surface of the porous membrane is glossy or lustrous, light irradiated on the test paper is reflected at a given rate irrespective of the color strength of the test paper. This increases white and color reflectivities to an extent corresponding to the gloss as shown in the following equation.

Reflectivity ratio=(white reflectivity+membrane glossiness)/(color reflectivity+membrane glossiness)

wherein membrane glossiness=constant.

More particularly, when the case where reflection takes place owing to membrane gloss is compared with the case where no reflection is ascribed to membrane gloss for the same degree of coloration of a test paper caused by a sample, i.e. for the same change in color reflectivity, both a numerator and a denominator in the above equation are inflated depending on the reflection ascribed to the membrane gloss, so that a change in reflectivity becomes small. Eventually, measuring sensitivity and accuracy for measurement values lower. Hence, the surface of the second layer should preferably be in a gloss and luster-free state.

The boundary between the first layer and the second layer is within a range of ⅕ to ½ of the thickness of the porous membrane from the surface of the first layer. In view of the relation between the large-sized pore portion and the small-sized pore portion, an average pore size of the first layer at the section of the porous membrane is larger than an average size of the second layer.

When the boundary between the first layer and the second layer is within such a range as defined above and the average pore size of the first layer is larger than the average size of the second layer, the object that should be filtered out in the sample can be separated by filtration at a position distant from the surface (measuring surface) of the second layer. Thus, it is favorable that such a reagent as indicated before can be carried in a satisfactory manner.

The thickness of the porous membrane is within a range of 50 to 200 μm, preferably 90 to 180 μm and most preferably 110 to 150 μm. The thickness of the porous membrane within such a range as indicated above is favorable for the reasons that satisfactory membrane strength is obtained, an influence by object that should be filtered out is lessened, a percolating time (developing time) of the sample is shortened and the amount of the sample required is allowed to be small.

Further, the porosity of the porous membrane ranges 60 to 95%, preferably 70 to 80%. The porosity of the porous membrane within such a range as indicated above is convenient for the reasons that a sample and a reagent can be satisfactorily carried and satisfactory membrane strength is obtainable.

It will be noted that the porosity (%) is obtained according to a weight method using the following equation Porosity (%)={1−(weight of dried membrane/specific gravity of membrane component)/volume of membrane}×100.

In the formula, the term "membrane" means porous membrane, and the specific gravity of membrane component means a specific gravity of a polymer for the porous membrane.

As stated hereinabove, the average pore size of the first layer at the section of the porous membrane is larger than that of the second layer, and the average pore size at openings in the surface of the first layer (i.e. an average pore size in the surface of the first layer) ranges 0.5 to 10 μm, preferably 1.0 to 5.0 μm. The average pore size at openings in the surface of the second layer (i.e. an average pore size in the surface of the second layer) ranges 0.1 to 3.0 μm, preferably 0.5 to 3.0 μm.

The average pore size in the surface of the first layer within the above range is favorable because a sample is able to rapidly infiltrate (percolate) and thus, no clogging with an object that should be filtered out occurs. The average pore size in the surface of the second layer within the above range is favorable because a sample is allowed to rapidly develop and thus the reagent can be carried satisfactorily.

Specific examples of the polymer used as a material for the porous membrane include nitro cellulose, polyvinyl difluoride, cellulose acetate, polysulfones, polyether sulfones, polyethylene and the like. Of these, polyether sulfones are preferred for the reason that when a reagent for use in blood glucose level measurement is carried, deterioration of the reagent with time is least likely.

It is preferred that the porous membrane is constituted of a material having hydrophilicity, so that a time of supplying and developing a sample can be shortened. On this account, it is preferred that a hydrophilicizing agent to be carried on the porous membrane. Also, it is preferred that a hydrophilicizing treatment of the porous membrane is carried out.

Specific examples of the hydrophilicizing agent include surface active agents such as Triton X-100 (Rohm & Haas Co.), water-soluble silicones, hydroxypropyl cellulose, polyethylene glycol, polypropylene glycol and the like. Preferred hydrophilicizing treatments include plasma treatment, glow discharge, corona discharge, UV irradiation and the like methods.

Further, aside from such reagents and hydrophilicizing agents as set out hereinabove, electrolytes (e.g. phosphates, phthalates, succinates, citrates, borates, and acetates), and organic substances (e.g. glycine and trishydroxymethylaminomethane) may be carried on the porous membrane, if desired.

The test paper of the invention formed of such a porous membrane as stated above is able to shorten a developing time of a sample and permits an object that should be filtered out in the sample to be filter out at a position distant from the surface (measuring surface) of the second layer, resulting in high measurement accuracy. Thus, the test paper is useful because of favorable use as a test paper for a chip for component measurement.

The test paper of the invention is not critical with respect to the shape thereof and may be selected, as required, from a circular shape, an elliptical shape, rectangular shapes such as a square, a rectangle, a rhombus and the like, a triangle, a hexagon, an octagon and the like.

Next, the porous membrane of the invention is now described in detail.

The porous membrane of the invention is one which can be used for formation of the test paper of the invention. More particularly, the porous membrane comprises a first layer having a surface and a second layer having another surface, wherein the first layer is made of large-sized pore portions, with a surface of the first layer being a smooth surface having apertures thereat, the second layer is made of small-sized pore portions, with a surface of the second layer having apertures thereat, and a boundary between the first layer and the second layer is located from the surface of the first layer within a range of ⅕ to ½ of a thickness of the porous membrane, and wherein a membrane thickness ranges 50 to 200 µm, a porosity ranges 60 to 95%, the first layer has an average pore size of 0.5 to 10 µm in the surface thereof, and the second layer has an average pore size of 0.1 to 3.0 µm in the surface thereof. That is, the porous film of the invention is not limited provided that it is a reagent-free membrane as selected from porous membranes forming such a test paper of the invention as having set forth hereinbefore.

The porous membrane of the invention should preferably have a ratio of an average pore size in the surface of the first layer to an average pore size in the surface of the second layer at 1 to 6 for the reason that development of a sample becomes rapid on use as a test paper, and more preferably 1 to 4.

Further, like the porous membrane forming the test paper of the invention as having set out hereinbefore, the porous membrane of the invention has the second layer whose surface preferably has a glossiness of not higher than 11, more preferably 3 to 10 and most preferably 3 to 8. So far as the surface glossiness of the second layer is within the above-defined range, the surface of the second layer has irregularities and is in a gloss and luster-free state. In a reflection absorbance measurement used as a test paper for colorimetry, direct light reflected at the surface serves as a noise, so that the surface of the second layer should preferably have irregularities and be in a gloss and luster-free state.

Next, a method of making porous membranes (a porous membrane forming a test paper of the invention and a porous membrane of the invention) is described in detail.

For the preparation of the porous membrane, wet process membrane formation is favorably shown. Aside from the wet process membrane formation, melt process membrane formation, dry process membrane formation and the like are known. Where anisotropic membrane of a type wherein a pore size in one surface differs from a pore size in other surface is made, it is preferred to use wet process membrane formation.

The wet process membrane formation includes a membrane-forming stock solution feed step of feeding a stock solution for film formation on a substrate as a membrane, an immersion-in-coagulation bath step of immersing the substrate, after the membrane-forming stock solution feed step in a coagulation bath, a rinsing step of removing a solvent component and/or a water-soluble additive component from the substrate, after the immersion-in-coagulation bath step, in a water bath, and a drying step of drying the substrate after the rinsing step.

The membrane-forming stock solution feed step is a step wherein a film-forming stock solution is applied onto a substrate as a membrane. More particularly, the step is one wherein film-forming stock solution is spread out on or coated over a substrate by use of a cast thickness adjustable applicator, or one wherein the stock solution is discharged from a T-die.

The film-forming stock solution contains a non-water soluble, first component polymer serving as a membrane component, and a water-soluble second component serving as a component to be extracted, in which the concentration of the first component polymer preferably ranges 12 to 15 wt %. It is preferred that the non-water soluble first component polymer and the water-soluble second component are contained, by which aggregation of polymer is suppressed, and pores are established at spaces created after removal of these components by extraction thereby improving a porosity.

Specific examples of the non-water soluble first component polymer include nitro cellulose, polyvinylidene fluoride, cellulose acetate, polysulfones, polyethylene, polyether sulfones and the like. Of these, polyether sulfones are preferred for such reason as set out hereinbefore; where a reagent used for blood glucose level measurement is carried, deterioration in reagent activity with time is least likely.

For the water-soluble second component, mention is made, for example, of polyvinylpyrrolidone, polyethylene glycol, polyacrylamide, polyacrylic acid, hydroxypropyl cellulose, methyl cellulose and the like, which are soluble in solvents described hereinafter and can be readily removed by extraction after the immersion-in-coagulation bath step described hereinafter. Of these, polyvinylpyrrolidone is preferrable because of such characteristic properties thereof that polyvinylpyrrolidone is not soluble in nitro cellulose, polyvinyl difluoride, cellulose acetate, polysulfones, polyethylene, polyether sulfones and the like, is dissolved in a polar solvent capable of dissolving these polymers, and can be removed by extraction with water after coagulation.

For the solvents of the membrane-forming stock solution used for the purpose of dissolving the first component polymer and the water-soluble second compound, mention is specifically made of organic polar solvents such as N-methyl-2- pyrrolidone (NMP), dimethylformamide, dimethylsulfoxide, dimethylacetamide and the like, of which N-methyl-2-pyrrolidone is preferable.

In the membrane-forming stock solution, the charge ratio between the first component polymer and the water-soluble second component is preferably in the range of 1:1 to 1:3. The reason why the charge ratio within this range is preferable is that the resultant second layer made of a small-sized pore portion occupies a portion corresponding to not less than a half of the membrane thickness in the porous membrane, is able to keep a porosity, and does not prevent a sample from percolating.

It will be noted that a cast thickness adjusted upon coating of the membrane-forming stock solution onto a substrate preferably ranges 70 to 260 nm because the thickness of the resulting porous membrane falls within such a preferred range as defined hereinbefore.

The substrate may be hitherto known ones and should preferably be those substrates having irregularities on a surface onto which a film-forming stock solution is coated. As such substrates, mention is favorably made of a glass sheet whose glossiness is 12 or below, a matted film having a glossiness of 12 or below, a glass sheet coated with a glareless polyethylene terephthalate film having a glossiness of 12 or below (e.g. a matted film having a glossiness of 12 or below). This is because the irregularities of the substrate are transferred to the surface of the second layer of the resulting porous membrane. It will be noted the glossiness used herein is determined based on JIS Z8741.

The immersion-in-coagulation bath step is a step wherein the substrate obtained after the membrane-forming stock solution feed step is immersed in a coagulation bath having water therein. More particularly, this step is one wherein the substrate onto which the membrane-forming stock solution has been coated is immersed in a coagulation bath to permit the first component polymer to be deposited on the substrate.

An example of the coagulation bath conveniently includes an aqueous coagulation bath containing a 60 to 85 w/w %, preferably 70 to 80 w/w % of a solvent for the membrane-forming stock solution. More particularly, an aqueous solution containing 60 to 85 w/w % of N-methyl-2-pyrrolidone is preferred. The content of a solvent within the above range ensures slow coagulation of the first component polymer, thereby forming a membrane having a porous structure.

When the concentration of a solvent in the membrane-forming stock solution in the coagulation bath is lower than 60 w/w %, there cannot be obtained an effect of adding a solvent to the stock solution. When the concentration exceeds 85 w/w %, no membrane is allowed to coagulate.

The immersion of the substrate in the coagulation bath is effected at a temperature of the coagulation bath ranging 10 to 50° C., preferably 20 to 40° C. for a time ranging 3 to 20 minutes, preferably 5 to 10 minutes. If the coagulation bath temperature is within this range, the deposition rate of the first component polymer becomes appropriate, thereby forming a membrane having a porous structure. In addition, when the immersion time is shorter than three minutes, all of first component polymer is not allowed to deposit and thus, no membrane is formed. When the time is longer than 20 minutes, no change in membrane structure occurs, thereby lowering a production efficiency.

The rinsing step is one wherein the substrate after the immersion-in-coagulation bath step is immersed in the water bath to remove the solvent component and/or the water-soluble additive component therefrom. More particularly, this step is one wherein the membrane formed by deposition of the first component polymer (hereinafter referred to simply as "membrane made of a first component polymer") is immersed in the water bath for 10 to 1000 minutes, preferably 15 to 60 minutes, thereby removing the solvent component and/or the water-soluble additive component (e.g. the above-mentioned solvent, and the above-mention water-soluble second component) by extraction.

The drying step is one wherein the membrane made of the first component polymer after the rinsing step is dried. More particularly, using natural drying, an electric oven or the like, a process of drying under conditions of 30 to 100° C., preferably 40 to 80° C. and one minute to 24 hours, preferably one minute to two hours may be mentioned.

The porous membrane obtained according to such a manufacturing method is useful as an anisotropic porous membrane which comprises a first layer having a surface at which a sample is supplied, a second layer having a surface at which the sample percolates up and is measured, and a boundary between the first layer and the second layer established within a range of ⅕ to ½ of a thickness of the porous membrane from the surface of the first layer.

EXAMPLES

The invention is more particularly described by way of examples, which should not be construed as limiting the invention thereto.

Examples 1 to 7, Comparative Examples 1 to 7

Porous membranes of Examples 1 to 7 and Comparative Examples 1 to 7 were, respectively, formed under the following conditions.

Initially, membrane-forming stock solutions indicated in Table 1 below were each fed to a substrate in the form of a line by means of a syringe and spread out by use of a cast thickness-adjustable applicator so as to make cast thicknesses indicated in Table 2 below.

The respective substrates over which the membrane-forming stock solutions were spread out were immersed in coagulation baths obtained under coagulation bath solvent concentrations and coagulation bath temperatures as indicated in Table 2 below and made of an N-methyl-2-pyrrolidone aqueous solution (NMP aqueous solution), thereby permitting a polyether sulfone serving as a first component polymer to be deposited. Thereafter, the membrane made of the polyether sulfone was immersed in a water bath to remove, by extraction, NMP used as the solvent component and polyvinylpyrrolidone used as the water-soluble second component, followed by drying in an oven at 60° C. to obtain each porous membrane.

The substrate used was a glass sheet coated with a glareless film (matted film) made of a polyethylene terephthalate (PET) and having a glossiness of 12 or below (JIS Z8741). As mentioned above, polyether sulfone (Sumikaexcel 5200P, made by Sumitomo Chemical Co., Ltd.) was used as a first component polymer, polyvinylpyrrolidone (Plasdone K29/32, ISP Co., Ltd.) was used as a water-soluble, second component), and N-methyl-2-pyrrolidone (BASF Ltd.) was used as a solvent.

For a porous membrane forming a test paper of Comparative Example 7, a commercially available membrane having an isotropic structure (Supor-450WE4, Pall Inc. of the United States)

TABLE 1

| Component | Commercial Name | Relative Proportion |
|---|---|---|
| Polyether sulfone | Sumikaexcel 5200P | 15 wt % |
| Polyvinylpyrrolidone | Plasdone K29/32 | 32 wt % |
| N-methyl-2-pyrrolidone | BASF NMP | 53 wt % |

TABLE 2

| | Cast Thickness (μm) | Solvent Concentration in Coagulation Bath (%) | Coagulation Bath Temperature (° C.) |
|---|---|---|---|
| Comp. Ex. 1 | 170 | 85 | 50 |
| Comp. Ex. 2 | 170 | 70 | 25 |
| Comp. Ex. 3 | 170 | 75 | 45 |
| Comp. Ex. 4 | 180 | 72.5 | 15 |
| Comp. Ex. 5 | 50 | 75 | 30 |
| Comp. Ex. 6 | 320 | 75 | 30 |
| Comp. Ex. 7 | 210 | 50 | 60 |
| Example 1 | 170 | 80 | 40 |
| Example 2 | 170 | 80 | 35 |
| Example 3 | 170 | 75 | 30 |
| Example 4 | 170 | 75 | 25 |
| Example 5 | 170 | 72.5 | 20 |
| Example 6 | 70 | 75 | 30 |
| Example 7 | 260 | 75 | 30 |

Individual membranes were subjected to the following methods to determine the average pore sizes in the surfaces of the first layer and the second layer, a ratio of an average pore size in the surface of the first layer to an average size in the surface of the second layer, a position of a boundary between the first and second layers, a membrane thickness, and a porosity. The results are shown in Table 3 below.

The average pore size in the surface was determined as follows: a surface of each porous membrane was shot with a scanning electron microscope (JSM-840, made by Japan Electronic Co., Ltd.), and the resulting image is analyzed with an image analyzer (IP-1000PC, made by Asahi Kasei Corporation) to calculate sizes of pores within the visual field as a circle equivalent diameter after conversion to area thereby providing an average pore size in the surface as a result of arithmetic average thereof. Using the resultant average pore sizes, the ratio of the average pore size in the surface of the first layer to the average pore size in the surface of the second layer was determined as an average pore size ratio.

In FIG. 1, there is shown an electron micrograph of a surface of a second layer of a porous membrane obtained in Example 3. This reveals that the second layer has irregularities formed on the surface thereof.

The position of the boundary was determined such that a frozen cleavage section of a porous membrane was shot with a scanning electron microscope (JSM-840, made by Japan Electron Co., Ltd.), and a large-sized pore portion and a small-sized pore portion were observed from the section density of the resulting image to determine a position of the boundary between the first layer and the second layer.

The measurement of the section density was carried out at individual divisions after division of a porous membrane into 10 parts along a thickness thereof. The section density was determined in such a way as set out hereinbefore, i.e. a membrane portion of an electron micrograph at a magnification of 1500 of a section of each porous membrane is taken in a scanner at 300 dpi on a 8 bits gray scale, the resulting image is binarized while taking an average value of scale values containing 5% of a black element from a black color side and also from white color side as a border line, thereby determining the density from a ratio of the white element.

Figure 2:
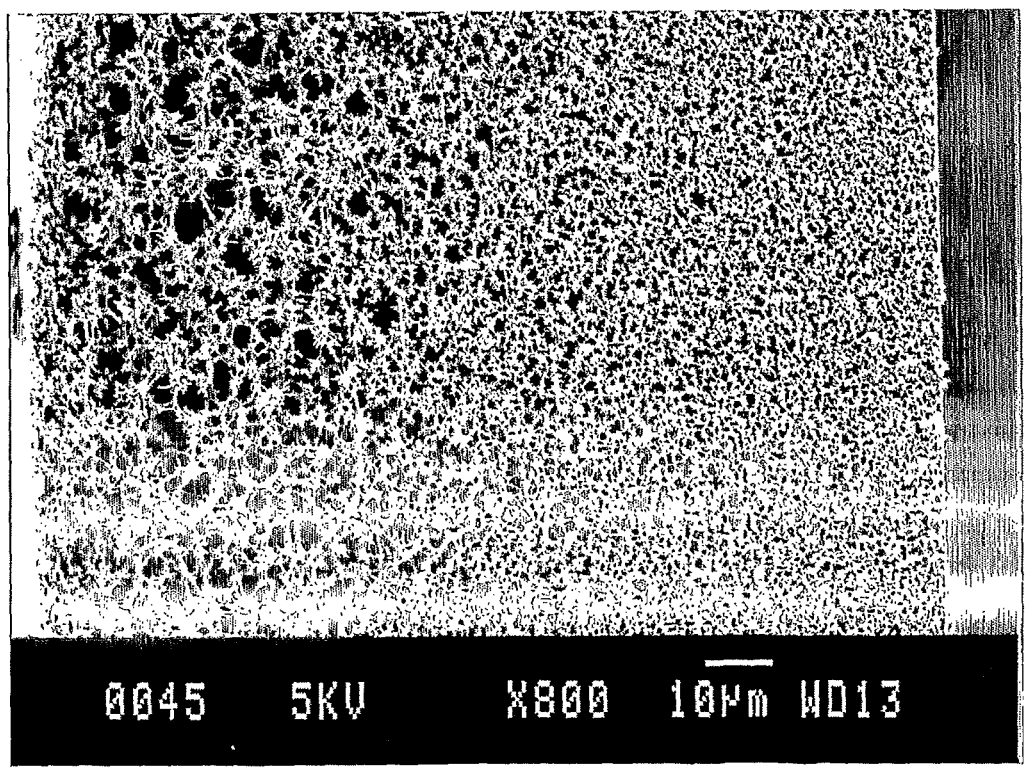
FIG. 2 is an electron micrograph showing a section of a frozen cleavage porous membrane obtained in Example 3.
Figure 3:
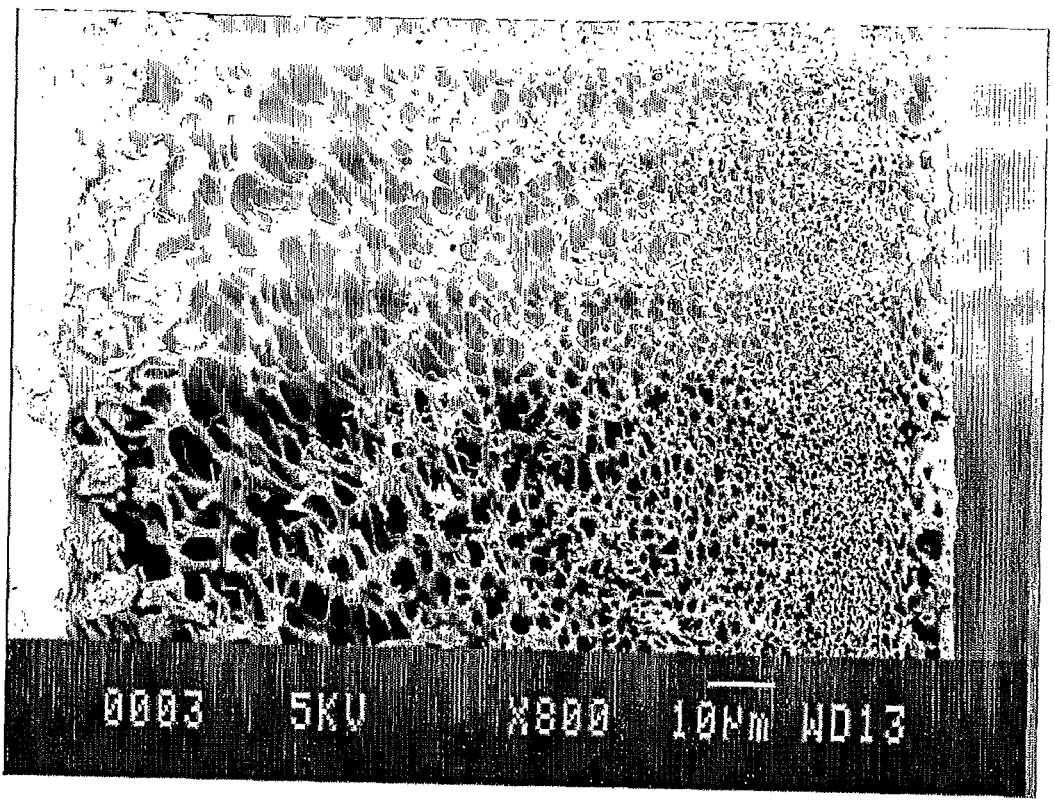
FIG. 3 is an electron micrograph showing a section of a frozen cleavage porous membrane obtained in Comparative Example 3.
Figure 4:
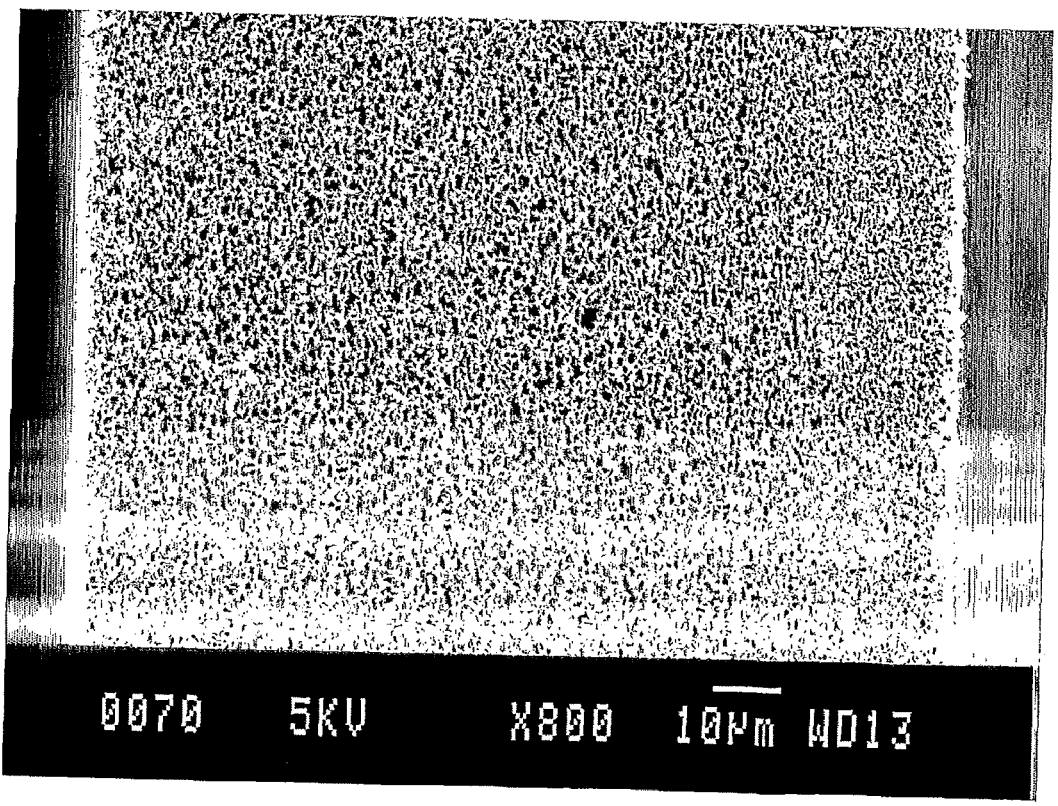
FIG. 4 is an electron micrograph showing a section of a frozen cleavage porous membrane obtained in Comparative Example 7.

FIG. 2 shows an electron micrograph showing a frozen cleavage section of a porous membrane obtained in Example 3, FIG. 3 shows an electron micrograph showing a frozen cleavage section of a porous membrane obtained in Comparative Example 3, and FIG. 4 shows an electron micrograph showing a frozen cleavage section of a porous membrane obtained in Comparative Example 7.

The membrane thickness was determined by measuring individual porous membranes with a micrometer (Mitutoyo Corporation).

The porosity (%) was determined according to a weight method using the following equation as illustrated hereinbefore Porosity (%)={1−(weight of dried membrane/specific gravity of membrane component)/volume of membrane}×100.

In the equation, the membrane means each porous membrane, and the specific gravity of membrane component is a specific gravity of a polymer constituting each porous membrane and, in the examples, a specific gravity of 1.37 of polyether sulfone was used.

TABLE 3

| | Average Pore Size in Surface of First Layer (μm) | Average Pore Size in Surface of Second Layer (μm) | Average Pore Ratio | Position of Boundary | Membrane Thickness (μm) | Porosity (%) |
|---|---|---|---|---|---|---|
| Comp. Ex. 1 | 15 | 5 | 3 | 1/2 | 110 | 95 |
| Comp. Ex. 2 | 0.3 | 0.04 | 7.5 | 3/10 | 140 | 55 |
| Comp. Ex. 3 | 2 | 0.8 | 2.5 | 7/10 | 110 | 81 |
| Comp. Ex. 4 | 2 | 0.8 | 2.5 | 1/10 | 135 | 72 |
| Comp. Ex. 5 | 2 | 0.8 | 2.5 | 1/2 | 35 | 73 |
| Comp. Ex. 6 | 2 | 0.8 | 2.5 | 1/2 | 250 | 88 |
| Comp. Ex. 7 | 0.5 | 0.5 | 1 | — | 140 | 84 |
| Example 1 | 10 | 3 | 3.3 | 1/2 | 120 | 90 |
| Example 2 | 5 | 1.5 | 3.3 | 1/2 | 125 | 88 |
| Example 3 | 2 | 0.8 | 2.5 | 2/5 | 130 | 74 |
| Example 4 | 0.5 | 0.1 | 5 | 3/10 | 135 | 65 |
| Example 5 | 2 | 0.8 | 2.5 | 1/5 | 120 | 77 |
| Example 6 | 2 | 0.8 | 2.5 | 1/2 | 50 | 88 |
| Example 7 | 2 | 0.8 | 2.5 | 1/2 | 200 | 84 |

Test Example 1

The following experiment was conducted using the porous membranes of Examples 1 to 7 and Comparative Example 1 to 7, but without carrying a reagent and a hydrophilicizing agent.

The respective porous membranes not carrying a reagent and a hydrophilicizing agent were each fixed on a sample holder of a spectrophotometer (UV-2400(PC)S, made by Shimadzu Corporation) so as to measure a reflection absorbance, to which 5 μl of a human blood was added to the surface of a first layer by use of a micropipette (made by Eppendorf Inc.) to measure a change of reflection absorbance with time on the surface of the second layer. A time ranging from the time when the rate of change in reflectivity in one second exceeded 1% of a final rate of change till the time when the range of change in reflectivity in one second is below 1% was taken as a developing time Δt. The results are shown in Table 4 below.

The final rate of change means a rate of change (rate of change 100%) between a reflectivity after lapse of a measuring time (260 seconds) and a reflectivity at the time of commencing the measurement (0 second).

It will be noted that measuring conditions are such that photometric value=reflectivity, wavelength=610 nm, slit width=2.0 nm, timing mode=automatic, measuring time=260 seconds, sampling pitch=0.1 second, number of cells=1, and the number of data=901.

Test Example 2

The following experiment was conducted using the porous membranes of Examples 1 to 7 and Comparative Examples 1 to 7. The porous membrane was carried thereon with the reagent and hydrophilicizing agent indicated below.

The respective porous membranes each having the reagent and hydrophilicizing agent carried thereon were each fixed on a sample holder of a spectrophotometer (UV-2400(PC)S, made by Shimadzu Corporation) so as to measure a reflection absorbance, to which 5 μl of a human blood was added to the surface of a first layer by use of a micropipette (made by Eppendorf Inc.) to measure reflection absorption spectra of reflection absorbance on the surface of the second layer. While comparing with the spectra of individual porous membranes per se, the presence or absence of influence of the blood pigment was determined. The results are shown in Table 4 below.

It will be noted that measuring conditions were such that photometric value=reflectivity, wavelength range (nm)=700 nm to 500 nm, scanning speed=moderate, slit width=2.0 nm, sampling pitch=1 nm.

For the reagent, there were used glucose oxidase (GOD), peroxidase (POD) and 4-aminoantipyrine, N-ethyl-N-(2-hydroxy-3-sulfopropyl)-m-toluidine (TOOS), and Triton X-100 was used as the hydrophilicizing agent.

In the carrying method of these reagents and hdyrophilicizing agent ordinarily employed conditions can be selected. In this example, the respective porous membranes were immersed in a phosphate buffer solution dissolving such a reagent and hydrophilicizing agent therein to coat the membrane with the reagent and hydrophilicizing agent, followed by drying to having the agents carried thereon.

The total amount (mg/cm$^2$) of the reagent and hydrophilicizing agent was determined by precisely measuring the weight of each porous membrane prior to carry of a reagent and a hydrophilicizing agent and the weight after the carry and calculating a difference in weight.

TABLE 4

| | Developing Time Δt (seconds) | Amount of reagent (mg/cm$^2$) | Influence of Blood Pigment |
|---|---|---|---|
| Comp. Ex. 1 | Impossible to measure owing to too weak membrane strength | | |
| Comp. Ex. 2 | >30 | 0.5 | No |
| Comp. Ex. 3 | 4.4 | 0.9 | Yes |
| Comp. Ex. 4 | 12.5 | 1.6 | No |
| Comp. Ex. 6 | 19.8 | 1.5 | No |
| Comp. Ex. 5 | Impossible to measure owing to too weak membrane strength | | |
| Comp. Ex. 7 | >30 | 2.2 | No |
| Example 1 | 25 | 0.9 | No |
| Example 2 | 3.3 | 1.1 | No |
| Example 3 | 4.7 | 1.1 | No |
| Example 4 | 6.3 | 1.0 | No |
| Example 5 | 6.8 | 1.3 | No |
| Example 6 | 3.2 | 0.9 | No |
| Example 7 | 7.1 | 1.2 | No |

Examples 8 to 11

PET films whose surface was subjected to sand blasting to provide irregularities on the surface as having glossiness of 2.9, 5.5 and 11.3, respectively, and a PET film having an ordinary gloss (a glossiness of 50) were, respectively, so attached to glass sheets such that the treated surface was faced up for those sand blasted and the non-treated PET film was attached as it is, followed by membrane formation under the same conditions as in Example 4 of Table 2, thereby providing porous membranes having a substrate side surface glossiness of 3 (Example 8), 6 (Example 9), 10 (Example 10) (using sand-blasted PET films in these examples), and 43 (Example 11) (using a non-treated PET film). These porous membranes were coated with the following reagents and provided for test.

Coated reagents: GOD, POD and 4-aminoantipyrine, N-ethyl-N-(2-hydroxy-3-sulfoprpyl)-m-toluidine (TOOS) Triton X-100 (hydrophilicizing agent)

Using the porous membranes after coating treatment, the following experiment was conducted.

Figure 5:
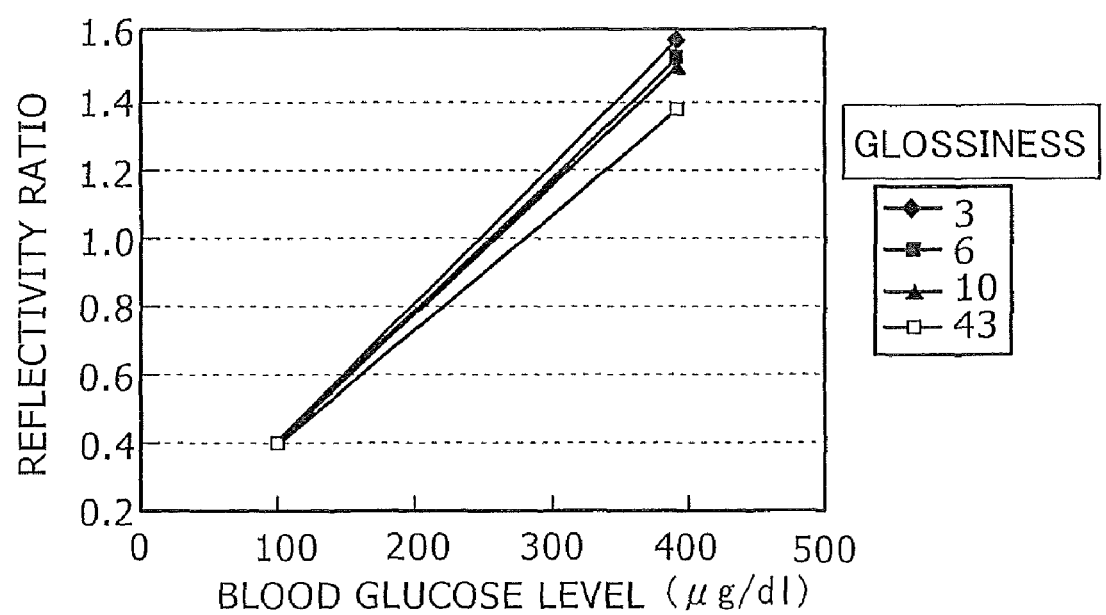
FIG. 5 is a graph showing calibration curves obtained from reflection absorbance measurement carried out by use of porous membranes of Examples 8 to 11

A porous membrane to be assessed was fixed on a sample holder of a spectrophotometer (UV-2400(PC)S, made by Shimadzu Corporation) so as to measure a reflection absorbance, to which 5 μl of a human blood, adjusted in blood glucose level to 100 μg/dl or 400 μg/dl, was added to the surface of a first layer by use of a micropipette (made by Eppendorf Inc.) to measure reflection absorption spectra of reflection absorbance on the surface of the second layer. Based on the results, an analytical curve was made from the relation between the blood glucose level and the reflectivity ratio to obtain a gradient thereof. FIG. 5 is a graph showing the analytical curve. The reflectivity ratios at the respective blood glucose levels and the gradients of the analytical curves are shown in Table 5.

TABLE 5

| | Example 8 | Example 9 | Example 10 | Example 11 |
|---|---|---|---|---|
| Glossiness | 3.0 | 6.0 | 10.0 | 43 |
| Blood Glucose Level at 100 | 0.39 | 0.39 | 0.39 | 0.39 |
| Blood Glucose Level at 400 | 1.56 | 1.52 | 1.50 | 1.36 |
| Gradient | 0.0039 | 0.0038 | 0.0037 | 0.0032 |

From these results, it was found that when the human blood having a blood glucose level of 400 μg/dl was measured, the porous membrane of Example 11 which had a glossiness of 43 lowered in reflectivity ratio when comparing with the porous membranes of Examples 8 to 10 having a glossiness of 3 to 10, with a smaller gradient of the analytical curve. The need for the measurement of blood glucose level is mainly for patients, such as diabetic patients, having a high blood glucose level, particularly, an elevated blood glucose level, for example, of 400 μg/dl. When a porous membrane having a glossiness of 11 or below, a measuring accuracy in such a high range of blood glucose level as mentioned above can be more improved.

INDUSTRIAL APPLICABILITY

The porous membrane of the invention can be used as a test paper of a chip for measuring a component in a blood measuring device. The test paper of the invention is useful for the reasons that it allows a sample to be developed at a high speed and is able to shorten the developing time. In addition, upon color measuring, an object that should be filtered out in a sample can be separated and removed by filtration and ensures an adequate amount of a reagent being carried, thereby enabling the measurement in higher accuracy.

Especially, a test paper having a second layer that has a glossiness of 11 or below at a surface thereof to which light is applied upon measurement of a reflection absorbance exhibits an excellent measuring accuracy in a range of high blood glucose level, for example, at about 400 μg/dl.

The invention claimed is:

1. A method of making a test paper for separating an object from a sample by filtration and for carrying thereon a reagent capable of giving a color by reaction with a specified component in the sample, the test paper comprising a porous membrane having a first surface on which the sample is applied and a second surface at which the sample is percolated and measured, the method comprising:

forming a membrane on a substrate by a single casting operation of a membrane-forming stock solution containing a non-water soluble first component polymer in which the concentration range is 12 to 15 wt % and a water-soluble second component polymer in which the concentration is a range of one to three times of the non-water soluble first component polymer;

treating the membrane formed by the single casting operation to form the porous membrane, wherein the porous membrane is formed to include a first layer having the first surface and a section density of 40% or less and a second layer having the second surface and a section density which exceeds 40%, and a boundary between the first layer and the second layer established within a range of 1/5 to 1/2 of a thickness of the porous membrane from the surface of the first layer; and wherein the first component polymer include at least one polymer selected from the group consisting of nitro cellulose, polyvinylidene fluoride, cellulose acetate, polysulfones, polyethylene and polyether sulfones, and wherein the second component polymer includes at least one polymer selected from the group consisting of polyvinylpyrolidone, polyethylene glycol, polyacrylamide, polyacrylic acid, hydroxypropyl cellulose, and methyl cellulose.

2. The method of claim 1, wherein the treating of the membrane further comprising rinsing the membrane to extract the water soluble second component.

3. The method of claim 1, wherein the treating of the membrane further comprises immersing the membrane in a coagulation bath.

4. The method of claim 3, wherein the coagulation bath comprises a solvent for the stock solution.

5. The method of claim 4, wherein the treating of the membrane further comprising rinsing the membrane to extract the solvent.

6. The method of claim 1, further comprising modifying the glossiness of a surface of the substrate prior to feeding the stock solution on the substrate.

7. The method of claim 6, wherein the modifying of the glossiness of the surface of the substrate comprises sandblasting the surface of the substrate.

8. The method of claim 1, wherein the average size of pores in the first surface is in the range of 0.5 to 10 μm and the average size of pores in the second surface is in the range of 0.1 to 3.0 μm.

* * * * *